Figure 1:
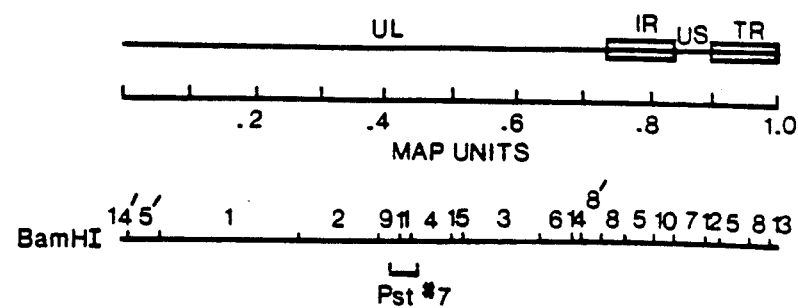

United States Patent [19]

Shih et al.

[11] Patent Number: 4,877,737

[45] Date of Patent: Oct. 31, 1989

[54] ATTENUATED PSEUDORABIES VIRUS WHICH HAS A DELETION IN AT LEAST A PORTION OF A REPEAT SEQUENCE AND VACCINE CONTAINING SAME

[75] Inventors: Meng-Fu Shih, San Diego; Mark D. Cochran, La Jolla; Richard D. Macdonald, San Diego, all of Calif.

[73] Assignee: PruTech Research and Development Partnership, San Jose, Calif.

[21] Appl. No.: 773,430

[22] Filed: Sep. 6, 1985

[51] Int. Cl.[4] .............................................. C12N 7/00
[52] U.S. Cl. ................................. 435/235; 435/172.1; 435/172.3; 435/236; 435/238; 435/948; 424/89; 935/29; 935/56; 935/57; 935/65
[58] Field of Search ............ 424/89; 435/172.1, 172.3, 435/235, 236, 238, 948; 935/29, 56, 57, 65

[56] References Cited

U.S. PATENT DOCUMENTS 4,514,497  4/1985  Kit et al. ........................... 424/89 X
4,680,176  7/1987  Berns et al. ...................... 435/236 X

FOREIGN PATENT DOCUMENTS 141458  5/1985  European Pat. Off. .

OTHER PUBLICATIONS

Post et al., PNAS, 77:4201–4205 (1980).
Koomey et al., J. Virol., 50:662–665 (1984).
Tenser et al., J. Clin. Microb., 17:122–127 (1983).
Price et al., Infection and Immunity, 34:571–580 (1981).
Thompson et al., Virology, 131:180–192 (1983).
Tenser et al., J. Gen. Virol., 64:1369–1373 (1983).
Gielkens et al., J. Gen. Virol., 66:69–82 (1985).
Lomniczi et al., J. Virol., 49:970–979 (1984).
Ben-Porat et al., Ninth International Herpesvirus Workshop, Seattle, Aug. 19–24, 1984.
L. E. Post et al., Cell 24, 555–565, 1981.
S. Kit et al., Herpesvirus Meeting, ICN–UCLA Symposium Abstract, Apr. 8–13, 1984.
S. Kit et al., Ninth International Herpesvirus Workshop, Seattle, Aug. 24–29, 1984.
B. Roizman et al., Cold Spring Harbor Conference on New Approaches to Viral Vaccines, Sep. 1983.
A. Tanaka et al., Herpesvirus Meeting, Keystone Company, 1984.

*Primary Examiner*—Robert J. Warden
*Assistant Examiner*—Robert Benson
*Attorney, Agent, or Firm*—John P. White

[57] ABSTRACT

Attenuated pseudorabies viruses are provided which comprise DNA including a sequence essential for replication of the attenuated virus, at least a portion of which is present in a sequence essential for replication of a naturally-occurring pseudorabies virus, from which at least a portion of a repeat sequence has been deleted. These viruses are useful as vaccines for immunizing animals against pseudorabies virus disease.

The invention also provides methods of preparing attenuated pseudorabies viruses.

13 Claims, 4 Drawing Sheets

ATTENUATED PSEUDORABIES VIRUS WHICH HAS A DELETION IN AT LEAST A PORTION OF A REPEAT SEQUENCE AND VACCINE CONTAINING SAME

BACKGROUND OF THE INVENTION

Within this application several publications are referenced by arabic numerals within parentheses. Full citations for these references may be found at the end of the specification immediately preceding the claims. The disclosures of these publications in their entireties are hereby incorporated by reference into this application in order to more fully describe the state of the art to which this invention pertains.

The ability to isolate viral DNA and to clone this DNA into bacterial plasmids has greatly expanded the approaches that can be used to make viral vaccines. The approach in this application is to modify the viral DNA sequence while in the cloned state in a plasmid, modifications which include, but are not limited to, insertion, deletion, or single or multiple base change. The modified DNA is then inserted back into the viral genome for the purpose of rendering the virus nonpathogenic. The resulting live virus product can be used to elicit an immune response and be protective as a vaccine, or in any other situation wherein a nonpathogenic virus infection of an animal is required.

One group of animal viruses, the herpesviruses or herpetoviridae, is an example of a class of viruses amenable to this approach. These viruses contain 100,000 to 150,000 base pairs of DNA as their genetic material, and several areas of the genome have been identified that are dispensible for the replication of virus in vitro in cell culture. Modification of these regions of the DNA are known to lower the pathogenicity of (to attenuate) the virus for the animal species. For example, inactivation of the thymidine kinase gene renders human herpes simplex virus non-pathogenic (1), and pseudorabies virus of swine non-pathogenic (2) and (3).

Removal of part of the repeat region renders human herpes simplex virus non-pathogenic (4) and (5). A repeat region has been identified in Marek's disease virus that is associated with viral oncogenicity and changes in this region correlates with lack of oncogenicity (6). These modifications in the repeat region do not teach the construction of attenuated pseudorabies viruses with deletions in repeat sequences. A different region in herpesvirus saimiri has similarly been correlated with oncogenicity (7). A region in pseudorabies virus has been shown to be deleted in naturally occurring vaccine strains (8). This deletion is partly responsible for lack of pathogenicity, however it does not occur in a repeat sequence and does not suggest attenuation resulting from a deletion in a repeat sequence.

The general conclusion from the literature is that herpesviruses contain nonessential regions of DNA in various parts of the genome, and that modification of these regions can lead to attenuation of the virus and derivation of a vaccine or non-pathogenic strain. The degree of attenuation of the virus is important in the utility of the virus as a vaccine. Deletions which cause too much attenuation of the virus will result in a vaccine that fails to elicit an adequate immune response.

The herpesviruses are known to cause a variety of latent and recurrent infections in human and other vertebrates and are even known to infect a fungus and an oyster. Among the conditions associated with herpesvirus infection are fever blisters caused by herpes simplex type 1, genital herpes caused by herpes simplex type 2, and chickenpox in children and shingles in adults caused by herpes zoster infection. A Class D herpes virus known as pseudorabies virus (PRV) induces Aujeszky's disease, an acute and often fatal nervous condition, in domestic and wild animals.

The natural host of pseudorabies virus is swine, in which infection is commonly inapparent but may be characterized by fever, convulsions and paralysis. Pseudorabies virus also infects cattle, sheep, dogs, cats, foxes and mink, where infection usually results in death of the host. The predominant visible feature of pseudorabies virus infection is intense pruritis generally resulting in host mutilation of the involved area. Violent excitement, fits and paralysis, all symptoms of encephalomyelitis, precede death which usually occurs within a few days following onset.

The pseudorabies virus genome has been mapped (See FIG. 1). The genome is known to include, in order, a unique long region, an internal inverted repeat sequence, a unique short region, and a terminal inverted repeat sequence.

Pseudorabies virus disease in swine is of serious concern by governmental bodies worldwide. In the U.S., infected swine cannot be sold except to slaughterhouses. Several individual states have separately enacted eradication control practices against pseudorabies. The R & D trend among traditional vaccine manufacturers has been to emphasize research leading to products that are based upon the subunit vaccine approach rather than using live viruses. This departure from live virus vaccines is due mainly to the recognized safety aspect of subunit vaccines, and their unlikelihood of containing infectious live viruses. It is well known that traditional live virus vaccines can revert to virulence which would seem to maintain a source of the disease during an eradication program. Attenuated pseudorabies viruses which have a deletion in at least a portion of a repeat sequence are a departure from most current live virus vaccines, and from the direction in which the vaccine industry as a whole is moving. These viruses suffer deletions in the repeat region and in other regions which cannot be repaired, i.e. the viruses cannot revert to virulence and are safe. A vaccine comprised of these viruses combines the safety aspect of subunit vaccines with the commercial and efficacious advantages of live virus vaccines.

Vaccines against pseudorabies virus are available. These vaccines are generally produced by the technique of cell culture attenuation. It is known that some live virus vaccines produced by this method contain deletions in the unique short region of the viral genome (8), however these viruses do not have deletions in repeat sequences.

On May 15, 1985 European Patent Publication No. 0 141 458 was published. This European Patent Publication is based upon European Patent Application No. 84201474.8, filed on October 12, 1984, and is entitled "Deletion Mutant of a Herpesvirus and Vaccine Containing Same".

This publication discloses the construction of attenuated pseudorabies viruses which have sequences of DNA deleted from the genome. Among the types of deletions are deletions in the unique short region and deletions in the repeat sequences. However this application does not provide enough detail to teach attenuating deletions in repeat sequences nor does it suggest the unexpected attenuating nature of deletions in repeat sequences. Specifically the inventors state that a small deletion in the repeat unit at the position of the Hind III site is not of importance for virulence in pigs, thereby indicating directly that they were not aware of the importance of the repeat region in attenuation. In any event, this application was published in a foreign country less than one year before the filing date of this application.

It is also known that deletions in the thymidine kinase (Tk) gene of the pseudorabies virus, located in the unique long region of the genome, renders the virus non-pathogenic but reduces the immune response in the host animal as well. U.S. Pat. No. 4,514,497, entitled "Modified Live Pseudorabies Viruses", discloses temperature resistant pseudorabies viruses which have deletions in the TK gene only and does not teach or suggest pseudorabies viruses which are attenuated by deleting portions of repeat sequences. In addition our attenuated pseudorabies viruses have never been selected for any kind of temperature resistance.

An ideal live virus vaccine is non-pathogenic and produces a strong immune response. It is therefore desirable to produce a live pseudorabies virus vaccine which would be non-pathogenic and produce a strong immune response in host animals.

This invention concerns attenuated pseudorabies viruses, i.e. pseudorabies viruses with lowered pathogenicity, which are useful as a vaccine to elicit a strong immune response or in other situations wherein a non-pathogenic viral infection of an animal is required. These viruses have a deletion in at least a portion of a repeat sequence. When used to immunize animals against pseudorabies virus disease, these viruses provide the advantages of not killing foreign animals or being passed to companion animals. Additionally, the viruses are stable, i.e. they do not revert to a pathogenic strain, and they provide a good immune response.

SUMMARY OF THE INVENTION

Attenuated pseudorabies viruses are provided which are comprised of DNA including a sequence essential for replication of the attenuated virus from which at least a portion of a repeat sequence has been deleted. At least a portion of the sequence essential for replication of the attenuated virus is present in a sequence essential for replication of a naturally-occurring pseudorabies virus. Vaccines comprised of an effective immunizing amount of a virus of this invention and a suitable carrier are useful for immunizing animals against pseudorabies virus disease.

The invention also provides methods of preparing attenuated pseudorabies viruses and methods of preparing pseudorabies virus vaccines from these viruses.

BRIEF DESCRIPTION OF THE FIGURES

FIG. 1 is a pseudorabies virus genome map including a BamHI restriction map showing the location of the PstI #7 fragment. UL=Unique long sequence; US=Unique short sequence; IR=Internal repeat sequence; TR=Terminal repeat sequence.

FIG. 2 is a pseudorabies virus BamHI #5 restriction map showing the location of the repeat deletion in S-PRV-001.

FIG. 3 (A) is a pseudorabies virus BamHI #5 restriction map showing the location of the repeat deletion in S-PRV-002 (B) is a pseudorabies virus PstI #7 restriction map showing the location of the deletion in the thymidine kinase gene region.

DETAILED DESCRIPTION OF THE INVENTION

The present invention concerns attenuated pseudorabies viruses. These viruses are comprised of DNA which includes a sequence essential for replication of the attenuated virus from which at least a portion of a repeat sequence has been deleted. At least a portion of this sequence is present in a sequence essential for replication of a naturally-occurring pseudorabies virus. The viruses are not temperature resistant, i.e. they have not been selected for replication at a temperature higher than temperatures which are permissive for the wild type. A virus which is not temperature resistant is defined herein as a virus capable of replicating only at temperatures permissive for the wild type. Additionally, the DNA sequence essential for replication of the attenuated virus may be derived from a naturally-occurring pseudorabies virus.

The deletion may be totally comprised of a portion of a repeat sequence or a portion of a repeat sequence and a portion of an adjacent unique region, i.e. the deletion may occur in a junction region. Additionally, a sequence nonessential for replication may be deleted from one or both repeats. Furthermore, at least a portion of the essential sequence of one repeat or one entire repeat may be deleted.

The invention also concerns attenuated pseudorabies viruses which are comprised of pseudorabies viral DNA from which at least a portion of a repeat sequence and a sequence not located within a repeat have been deleted. In one embodiment of the invention a nonessential sequence present in both repeats and a sequence not located within a repeat have been deleted. In a preferred embodiment of the invention the deleted sequence not located within a repeat is at least a portion of a gene. In a specific embodiment of the invention the deleted sequence not located within a repeat is at least a portion of the gene encoding pseudorabies thymidine kinase. An attenuated pseudorabies virus with a deletion in both repeats and a deletion in the gene encoding pseudorabies thymidine kinase has been constructed. This virus is designated S-PRV-002 and is deposited under ATCC Accession No. VR 2107.

The invention also concerns an attenuated pseudorabies virus which comprises pseudorabies viral DNA from which at least a portion of a repeat sequence other than the junction region or the immediate early genes has been deleted. An attenuated pseudorabies virus with a deletion in both repeat sequences upstream of the promoter for the immediate early genes has been constructed. This virus has been designated S-PRV-001 and is deposited under ATCC Accession No. VR 2106.

The invention also concerns vaccines for pseudorabies virus disease. These vaccines are comprised of an effective immunizing amount of an attenuated pseudorabies virus having at least a portion of a repeat sequence deleted and a suitable carrier. Typically the suitable carrier is a physiologically balanced culture medium containing stabilizing agents, e.g. sugars, salts and proteins. In one embodiment of the invention the vaccine for a swine contains an effective immunizing amount of an attenuated pseudorabies virus equal to about $10^3$ to about $10^9$ plaque forming units (pfu) per dose, while the effective immunizing amount for a dog, cat, sheep or bovine animal, i.e. cattle, is from about $10^4$ to about $10^6$ pfu per dose.

The invention also concerns methods of immunizing animals against pseudorabies virus disease by administering to the animals a suitable dose of a vaccine of this invention. The vaccine may be administered by intramuscular, subcutaneous, interperitoneal or intravenous injection. Additionally, the vaccine may be administered intranasally or orally.

The invention also concerns a method of preparing attenuated pseudorabies viruses. This method involves isolating wild type pseudorabies viral DNA and using restriction enzyme digestion to produce DNA restriction fragments. These restriction fragments are purified by agarose gel electrophoresis to obtain specific DNA fragments which are treated with appropriate enzymes, known to those skilled in the art, to produce modified viral DNA fragments. These modified viral DNA fragments are capable of binding to bacterial plasmid DNA sequences. Suitable bacterial plasmids are separately treated with appropriate restriction enzymes, known to those skilled in the art, to produce bacterial plasmid DNA sequences capable of binding to modified viral DNA fragments. These bacterial plasmid DNA sequences are then combined with the modified viral DNA fragments under suitable conditions to allow the viral DNA to bind to the bacterial DNA and form a viral-bacterial plasmid.

The viral-bacterial DNA plasmid is then mapped by restriction enzymes to generate a restriction map of the viral DNA insert. The viral-bacterial DNA plasmid is then treated with restriction enzymes known in the art to cause at least one deletion in the viral DNA sequence of the viral-bacterial DNA plasmid. This plasmid, containing at least one deletion in the viral DNA sequence, is transfected with wild type intact pseudorabies viruses into animal cells. The animal cells are maintained under suitable conditions to allow the wild type pseudorabies viral DNA to regenerate the wild type virus and a small percentage of viruses which have recombined with the viral DNA sequence of the plasmid. Some of these recombined viruses have deletions in their genome as a result of deletions in the viral DNA insert of the plasmid. These viruses are identified and subsequently plaque purified away from the wild type virus.

In a preferred embodiment of the invention the viral DNA restriction fragment inserted into the bacterial plasmid includes at least a portion of a repeat sequence. In a specific embodiment of the invention the deletion in the viral DNA sequence of the viral-bacterial DNA plasmid leads to deletions in both repeat sequences of the recombined virus. In another preferred embodiment of the invention the viral DNA restriction fragment inserted into the bacterial plasmid includes the gene encoding pseudorabies thymidine kinase. A specific embodiment of the invention involves deletions in the viral DNA sequence of the viral-bacterial DNA plasmids which lead to deletions in both repeat sequences and the gene encoding pseudorabies thymidine kinase of the recombined virus.

The invention also concerns methods of preparing pseudorabies virus vaccines. These methods include cultivating the viruses in roller bottles or a suspension of microcarrier beads, e.g. Sephadex ® beads. The viruses may also be cultivated by batch fermentation.

CONSTRUCTION OF ATTENUATED PSEUDORABIES VIRUSES

Materials and Methods

All methods employed are those in standard usage in molecular biology research laboratories or minor variations of those methods.

The starting wild-type pseudorabies virus for all these studies was the Shope strain obtained from the USDA, which is a virulent virus recommended for use in challenge studies. The virus was propagated less than 4 times in Vero cells for challenge stocks, and less than 10 times for the manipulation and purification of vaccine strains.

All enzymes employed are readily available from commercial sources and were used according to the recommendations of the suppliers. For example, restriction enzymes were obtained principally from New England Biolabs (Biolabs), Bethesda Research Laboratories (BRL), and IBI Corporation, among others. Bal 31 nuclease was from BRL; DNA T4 ligase was from Biolabs; calf-intestine phosphatase was from Boehringer-Mannheim Corp.; and the Klenow fragment of *E.coli* DNA polymerase I was from Biolabs.

Plasmid DNA was prepared essentially by the methods described in (10). Viral DNA preparation is described in (11). DNA preparations from small samples of plasmid transformed cells ("Mini preps") were made according to the methods described in (10).

DNA fragments were purified from agarose gels following electrophoretic resolution according to (10). Phenol extraction was used for low melting point agarose gels and electro-elution for regular agarose gels. DNA was transformed into *E.coli* strain HB101 by methods described in (10). DNA was transfected into animal cells essentially by he method of (12) and (13).

The structure and order of restriction fragments in DNA was analyzed by restriction digestion, resolution of the fragments by agarose gel electrophoresis and hybridization to defined radiolabeled DNA or RNA probes following transfer of restriction fragments from the gel to filters by a blot procedure ("Southern blot" analysis) described in (10). Viruses obtained from tissue culture monolayers infected with pseudorabies recombinant viruses were selected for the presence of the thymidine kinase genes in HAT medium, or the absence of the gene in Budr medium in procedures described in (14). The presence of the thymidine kinase enzyme was assayed by the $C^{14}$ thymidine labeling methods described in (15).

Restriction fragments of DNA were rendered blunt using the Klenow fragment of *E.coli* DNA polymerase as described in (10). Removal of terminal phosphate residues by digestion with calf-intestine phosphatase is also as described in (10).

Construction of S-PRV-001

The manipulations that resulted in a pseudorabies virus with a deletion in the repeat region were as follows. The thymidine kinase region of pseudorabies virus Shope strain was cloned as the 4300 bp PstI #7 fragment (pSY344). Contained within this region is an approximate 3200 bp BamHI fragment called Bam #11. The Bam #11 fragment has been reported to contain the pseudorabies virus thymidine kinase gene by marker rescue experiments and sequencing data (16). We have also shown by marker rescue experiments that our Bam

11 clone rescues a thymidine kinase pseudorabies mutant and thus contains the thymidine kinase gene.

Figure 2:
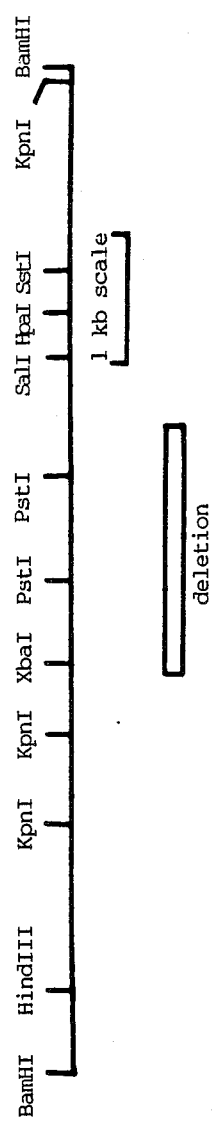
Figure 3A:
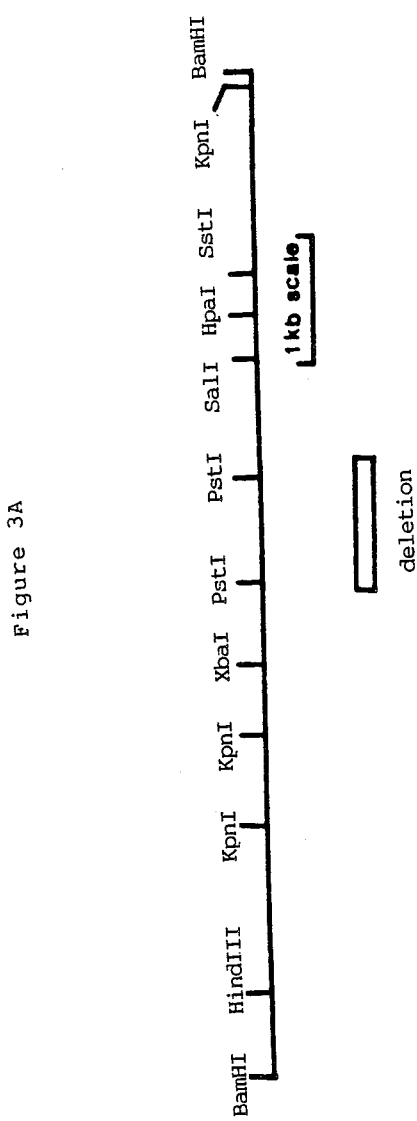
Figure 3B:
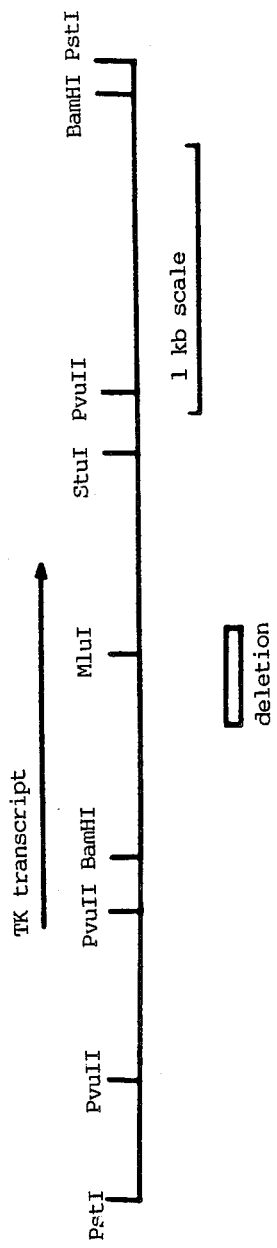

The MluI site lies within the thymidine kinase structural gene (16). Plasmids containing this insert were cut, digested and religated to create deletions at the MluI site. Plasmids were analyzed for the size of the deletion, and a plasmid with a deletion of approximately 300 bp (pSY513) was used in transfection in the presence of wild type pseudorabies virus DNA in animal cells. Viruses were selected in the presence of the drug bromodeoxyuridine. Candidate recombinant viruses were plaque purified away from wild type pseudorabies, a preparation of DNA was made, and the DNA was analyzed by restriction digestion and Southern blotting (10) to prove that a deletion was present in the viral genome. From these results, the location of the deletion in BamHI #5 has been determined and is shown in FIG. 2. By these methods a pseudorabies virus (S-PRV-001) was isolated which had suffered a deletion in both copies of BamHI #5 fragment and no deletion in Pst #7 fragment. The virus retains an intact and active thymidine kinase gene as determined by 14C-thymidine incorporation assay.

Construction of S-)PRV-002

An attenuated pseudorabies virus containing multiple deletions in the genome as a result of homologous recombination between cloned fragments of pseudorabies DNA and intact wild type pseudorabies DNA has been constructed. The methodology was as described in the construction of S-PRV-001.

The plasmid clone used in the recombination was derived from the PstI #7 cloned fragment of pseudorabies virus. It should be noted that while the cloned PstI #7 fragment maps to the long unique region, it is also weakly homologous to BamHI #5 repeat fragment. The PstI #7 fragment was purified from a PstI digest of viral DNA following agarose gel electrophoresis and was cloned into the Pst site of pBR 322 to form pSY344.

Deletions were made in this plasmid around the MluI site bY cutting plasmid DNA with MluI restriction enzyme followed by Ba131 nuclease digestion. The DNA was digested for varying lengths of time (10 to 60 seconds), samples were analyzed by agarose gel electrophoresis to determine the approximate extent of digestion. Samples digested between 100 and 2000 Base pairs were religated to circularize the DNA and transformed into *E.coli*. Plasmid pSY513 with a deletion of approximately 300 base pairs was used for recombination with viral DNA. The plasmid DNA was mixed with intact pseudorabies virus DNA and the mixture was transfected into rabbit skin cells. The expected location of deletions would be in regions of the DNA homologous to the plasmid DNA; i.e., in PstI #7 (or BamHI #11 contained there) and in BamHI #5 which hybridizes to a limited extent with PstI #7 fragment. The viruses recovered from transfection were selected with the drug bromodeoxyuridine which would select for recombinants that were defective in thymidine kinase activity. The thymidine kinase gene resides on fragment PstI #7 and a deletion in the gene would result from homologous recombination at that site. The viruses were plaque purified two times and examined for changes in the DNA by restriction mapping.

A pseudorabies virus recombinant called S-PRV-002 was shown by Southern hybridization to contain a deletion in BamHI #11 fragment and in BamHI #5 fragment (See FIG. 3). This virus is lacking in thymidine kinase activity, as shown by a 14C-thymidine incorporation assay described in (15).

Animal Trials Conducted With S-PRV-001 and S-PRV-002

The first set of studies was designed to compare the safety (virulence) and antigenicity (induction of antibody response) of S-PRV-001 and S-PRV-002 with wildtype pseudorabies virus (PRV).

Weaned pigs (4–6 weeks old) that had no prior exposure to PRV were inoculated with various concentrations of the above 3 viruses. The animals were observed daily for 14 days to detect clinical signs of PRV and body temperatures were recorded daily. At designated times, blood samples were taken from the pigs and the serum was tested for antibody to PRV, using a radioimmunodiffusion enzyme-linked immunosorbent assay (RIDEA). At various times post-inoculation, pigs were sacrificed, tissues were removed and assayed for the presence of virus.

The virulence of these three viruses was also evaluated by injecting young mice and determining the lethal dose level.

Results of these studies are presented in Tables 1–4.

TABLE 1

MOUSE VIRULENCE OF WILD-TYPE, S-PRV-001 OR S-PRV-002 PSEUDORABIES VIRUSES

| Virus | Virus Concentration | No. Dead/ No. Inoc. | Mean Death Time (Hrs.) | Clinical Signs |
|---|---|---|---|---|
| Wild-Type | $10^5$ | 4/4 | 62 | lethargic |
| | $10^4$ | 5/5 | 82 | severe pruritis |
| | $10^3$ | 4/5 | 86 | rough coat |
| | $10^2$ | 0/5 | — | |
| | $10^1$ | 0/5 | — | |
| S-PRV-001 | $10^6$ | 5/5 | 83 | lethargic |
| | $10^5$ | 5/5 | 94 | slight pruritis |
| | $10^4$ | 4/5 | 106 | moribund |
| | $10^3$ | 2/5 | 153 | |
| | $10^2$ | 0/4 | — | |
| S-PRV-002 | $10^6$ | 0/4 | — | none |
| | $10^5$ | 0/5 | — | |
| | $10^4$ | 0/4 | — | |
| | $10^3$ | 0/4 | — | |
| | $10^2$ | 0/4 | — | |

[a]Tissue culture infective dose$_{50}$; $TCID_{50}$

TABLE 2

SWINE VIRULENCE OF WILD-TYPE, S-PRV-001 OR S-PRV-002 PSEUDORABIES VIRUSES

| Virus | Virus Concentration[a] | Pig No. | Elevated Temp.[b] | CNS Signs[c] | Other Signs |
|---|---|---|---|---|---|
| Wild-Type | $10^2$ | 3 | + | + | Sneezing |
| | | 4 | ++ | + | — |
| | $10^4$ | 5 | +++ | ++ | — |
| | | 6 | + | +++ | weak, depressed |
| | | 7 | ++ | +++ | weak, depressed |
| | $10^6$ | 8 | ++ | +++ | weak, depressed died |
| | | 9 | + | ++ | — |
| | | 10 | +++ | ++ | — |
| S-PRV-001 | $10^4$ | 13 | ++ | ++ | weak, depressed |
| | | 17 | ++ | + | sneezing, coughing |
| | | 21 | + | — | — |
| | $10^5$ | 12 | + | — | — |

TABLE 2-continued

SWINE VIRULENCE OF WILD-TYPE,
S-PRV-001 OR S-PRV-002
PSEUDORABIES VIRUSES

| Virus | Virus Concentration[a] | Pig No. | Elevated Temp.[b] | CNS Signs[c] | Other Signs |
|---|---|---|---|---|---|
| | | 14 | + | — | — |
| | | 15 | + | — | — |
| | $10^6$ | 16 | + | — | — |
| | | 18 | ++ | — | snezzing, coughing |
| | | 20 | + | — | — |
| S-PRV-002 | $10^2$ | 25 | — | — | — |
| | | 26 | — | — | — |
| | $10^4$ | 27 | — | — | — |
| | | 28 | — | — | — |
| | | 29 | — | — | — |
| | $10^6$ | 30 | — | — | — |
| | | 31 | — | — | — |
| | | 32 | — | — | — |

[a] $TCID_{50}$
[b] elevated rectal temperatures presented as + - 105-106°, ++ - 106-107°, +++ - 107-108°.
[c] CNS signs included + - slight ataxia and stiffness of rear legs; ++ - A severe ataxia of rear legs, slight loss of balance; +++ - severe ataxia in all legs, incoordination, lateral recumency and continued head movements.

TABLE 3

SEROLOGIC RESPONSES OF PIGS
INOCULATED WITH WILD-TYPE,
S-PRV-001 or S-PRV-002 PSEUDORABIES VIRUSES

| Virus | Virus Concentration[a] | Pig No. | Antibody Titer[b] Day 14 | Day 21 | Day 28 |
|---|---|---|---|---|---|
| Wild-Type | $10^2$ | 3 | 32 | 32 | 32 |
| | | 4 | 64 | >64 | >64 |
| | $10^4$ | 5 | 32 | 64 | 32 |
| | | 6 | —[c] | — | — |
| | | 7 | 64 | >64 | 64 |
| | $10^6$ | 8 | —[c] | — | — |
| | | 9 | 64 | >64 | >64 |
| | | 10 | >64 | >64 | >64 |
| S-PRV-001 | $10^4$ | 13 | —[c] | — | — |
| | | 17 | 64 | >64 | >64 |
| | | 21 | >64 | >64 | >64 |
| | $10^5$ | 12 | —[c] | — | — |
| | | 14 | >64 | >64 | >64 |
| | | 15 | >64 | >64 | >64 |
| | $10^6$ | 16 | — | — | — |
| | | 18 | >64 | >64 | >64 |
| | | 20 | 64 | >64 | >64 |
| S-PRV-002 | $10^2$ | 25 | 8 | 8 | 4 |
| | | 26 | 8 | 8 | 4 |
| | $10^4$ | 27 | 64 | NT | 32 |
| | | 28 | 64 | 32 | 16 |
| | | 29 | 32 | 16 | 8 |
| | $10^6$ | 30 | 64 | 32 | 16 |
| | | 31 | 16 | 16 | 8 |
| | | 32 | 32 | 16 | 16 |

[a] $TCID_{50}$
[b] RIDEA test; all pigs were <2 on Day 0
[c] These pigs were sacrificed prior to Day 14
NT = Not tested

TABLE 4

VIRUS ISOLATION FROM PIGS
INOCULATED WITH WILD-TYPE,
S-PRV-001 or S-PRV-002 PSUEDORABIES VIRUSES

| Virus | Virus Concentration[a] | Pig No. | Day of Sacrifice[b] | Tonsil | Cerebrum | Mid-Brain | Spinal Cord | Kidney Liver Lung Spleen |
|---|---|---|---|---|---|---|---|---|
| Wild-Type | $10^2$ | 3 | 28 | —[c] | — | — | — | — |
| | | 4 | 28 | — | — | — | — | — |
| | $10^4$ | 5 | 28 | — | — | — | — | — |
| | | 6 | 12 | + | — | — | — | — |
| | | 7 | 28 | — | — | — | — | — |
| | $10^6$ | 8 | 10 | + | + | + | — | — |
| | | 9 | 28 | — | — | — | — | — |
| | | 10 | 28 | — | — | — | — | — |
| S-PRV-001 | $10^4$ | 13 | 12 | — | — | — | — | — |
| | | 17 | 28 | — | — | — | — | — |
| | | 21 | 28 | — | — | — | — | — |
| | $10^5$ | 12 | 5 | + | + | + | — | — |
| | | 14 | 28 | — | — | — | — | — |
| | | 15 | 28 | — | — | — | — | — |
| | $10^6$ | 16 | 5 | — | — | — | — | — |
| | | 18 | 28 | — | — | — | — | — |
| | | 10 | 28 | — | — | — | — | — |
| S-PRV-002 | $10^2$ | 25 | 28 | — | — | — | — | — |
| | | 26 | 28 | — | — | — | — | — |
| | $10^4$ | 27 | 28 | — | — | — | — | — |
| | | 28 | 28 | — | — | — | — | — |
| | | 29 | 28 | — | — | — | — | — |
| | $10^6$ | 30 | 28 | — | — | — | — | — |
| | | 31 | 28 | — | — | — | — | — |
| | | 32 | 28 | — | — | — | — | — |

[a] $TCID_{50}$
[b] Days post-inoculation
[c] Samples were scored negative after 2 passages in cell culture; all positive samples occured on first cell culture passage.

Wild-type PRV exhibited a mouse $LD_{100}$ of $10^{3.2}$ $TCID_{50}$. The mice were lethargic, had rough coats and pruritis (itching) prior to death. All pigs inoculated with wild-type PRV had an increase in body temperature and showed central nervous system manifestations typical of PRV infection. Virus was recovered from tissues of a pig sacrificed 10 days post-inoculation and from another pig sacrificed 12 days post-inoculation. By 14 days post-inoculation all of the pigs had PRV antibody which persisted at high levels through the 28-day sampling period.

The mouse $LD_{100}$ of S-PRV-001 was $10^{3.8}$ $TCID_{50}$; four times more virus was required to kill all of the mice than was required by wild type. The mean death time of the mice was delayed by 1 to 2 days, indicating this virus had lost some of its virulence for mice. Among the 9 pigs inoculated with S-PRV-001 all had an increase in temperature, but only 2 of the 9 pigs developed CNS signs and these were less severe than observed in pigs inoculated with wild-type virus. Virus was isolated from 1 of 2 pigs sacrificed 5 days post-inoculation. All of these pigs had PRV antibody levels equal to those from wild-type inoculated pigs.

S-PRV-002 was not virulent for mice and caused no clinical signs or febrile response in pigs. Virus could not be recovered from pigs sacrificed at 28 days postinoculation (no pigs were sacrificed earlier). The virus replicated well in the pigs as evidenced by the antibody levels, which were only slightly lower than measured in the wild-type and S-PRV-001 inoculated pigs.

The conclusions from these studies are that S-PRV-001 is a very good antigen but the deletion made was not adequate to provide a safe virus for use in pigs. On the other hand S-PRV-002 was avirulent in pigs and mice yet still retained its ability to induce a strong antibody response in pigs.

To test further the utility of S-PRV-002 as a vaccine virus, a vaccination/challenge study was conducted in 5–6 week old PRV antibody-free pigs. One group of pigs was reserved as challenge controls. The vaccinated pigs were observed as described above for adverse reaction following vaccination. At 27 days following vaccination, the vaccinated and control pigs were challenged by intranasal administration of $10^{4.7}$ $TCID_{50}$ of virulent virus. The pigs were observed an additional 14 days for signs of PRV infection.

The results of this study are presented in Table 5.

TABLE 5

SEROLOGIC AND CLINICAL RESPONSES FOLLOWING VACCINATION WITH S-PRV-002 AND CHALLENGE WITH WILD-TYPE PRV

| | | Post-Vaccination | | | | Post-Challenge | | | | |
|---|---|---|---|---|---|---|---|---|---|---|
| Study Group | Pig No. | Elev.[a] Temp. | CNS[b] Signs | Antibody[c] Day 14 | Antibody[c] Day 21 | Elev. Temp. | CNS Signs | Death | Antibody Day 7 | Antibody Day 14 |
| | 1 | — | — | 4 | 8 | — | — | +[d] | — | — |
| Vaccinates | 2 | — | — | 32 | 32 | — | — | — | >64 | >64 |
| | 3 | — | — | 2 | 2 | + | — | — | >64 | >64 |
| | 4 | — | — | 16 | 8 | + | — | — | >64 | >64 |
| | 9 | — | — | <2 | <2 | +++ | +++ | + | —[e] | — |
| Controls | 10 | — | — | <2 | <2 | +++ | +++ | + | —[e] | — |
| | 11 | — | — | <2 | <2 | +++ | + | — | <2 | >64 |
| | 12 | — | — | <2 | <2 | ++ | +++ | + | —[e] | — |
| | 13 | — | — | <2 | <2 | ++ | — | — | <2 | >64 |

[a]elevated temperature + = 105–106°, ++ = 106–107°, +++ = 107–108°
[b]CNS signs included + slight ataxia and stiffness of rear legs; ++ - A severe ataxia of rear legs, slight loss of balance, +++ - severe ataxia in all legs, incoordination, lateral recumbency and continued head movements.
[c]RIDEA test
[d]Pig died of causes other than PRV
[e]Pig died prior to day 7

Adverse post-vaccinal reactions, as evidenced by a rise in body temperature or demonstration of typical PRV signs, were not seen in the vaccinated animals. All vaccinates developed PRV antibody and the non-vaccinated controls remained seronegative. Following challenge with virulent virus, 3 of 5 control pigs had fevers, developed severe CNS signs and died. One control developed a fever, exhibited transient CNS signs and recovered. The fifth control developed a fever but did not show clinical signs of PRV infection. In contrast, 3 of the 4 vaccinated pigs remained clinically normal, and developed a strong secondary antibody response. Once vaccinated pig died 4 days post-challenge without showing clinical signs of PRV. Examination of tissue did not reveal lesions of PRV infection and no virus could be isolated. The cause of death remains unknown.

The conclusion from this study is that when S-PRV-002 is given at a dosage of $10^{4.0}$ $TCID_{50}$, it will elicit a strong protective response in the vaccinated animals. This response is adequate to prevent infection that kills 60% of non-vaccinated pigs.

Additional Pseudorabies Virus Constructions

Additional pseudorabies virus constructions with deletions in repeat sequences have been made according to the methods of this disclosure. One construction has a deletion comprised of a 2000bp sequence of DNA from the internal repeat and a 1000bp sequence from the adjacent unique long region. Results from preliminary tests of this virus in mice and pigs show that it is attenuated. This virus is an example of an attenuated pseudorabies virus with a deletion in a junction region, and is potentially useful as a vaccine for pseudorabies virus disease.

In another example, a pseudorabies virus with a deletion in the repeat region, specifically between the XbaI site and the HpaI site in BAMHI #5 fragment shown in FIG. 2, has been constructed. This virus has not yet been tested for virulence.

These examples show that other deletions in repeats can be constructed and indicate that deletions in the repeat sequences attenuate the virus.

References

1. R. W. Price and A. Kahn, Infection and Immunity 34, 571–580, 1981.
2. P. B. Tenser, et al , Journal of General Virology 64, 1369–1373, 1983.
3. S. Kit, et al., Ninth International Herpesvirus Workshop, Seattle, August 24–29, 1984.
4. Roizman, et al., Coldspring Harbor Conference on New Approaches to Viral Vaccines, September, 1983.
5. R. L Thompson, et al., Virology 131, 180–192, 1983.

6. A. Tanaka, et al., Herpesvirus Meeting, Keystone, Co., 1984.
7. J. M Koomey, et al., Journal of Virology 50, 662–665, 1984.
8. B. Lomniczi, et al., Journal of Virology 49, 970–979, 1984.
9. Ben-Porat, et al., Ninth International Herpesvirus Workshop, Seattle, August 24–19, 1984.
10. Maniatis, et al., Molecular Cloning: A Laboratory Manual, Cold Spring Harbor Laboratory Press, 1982.
11. L. E. Post, et al., PNAS 77, 4201–4205, 1980.
12. P. Dierks, et al., Developmental Biology Using Purified Genes.
13. D. D. Brown and C. F. Fox (Eds.) ICN-UCLA Symposium on Molecular and Cellular Biology, Acad. Press N.Y., pp. 347–366, 1981.
14. L. E. Post, Mackem, and B. Roizman, Cell 24, 555–565, 1981.
15. Tenser, et al., J. Clinical Microbiology 17, 122–127, 1983.
16. S. Kit, et al., Herpesvirus Meeting, ICN-UCLA Symposium, April 8–13, 1984, Abstract #1288.

What is claimed is:

1. An attenuated pseudorabies virus designated S-PRV-001 and deposited under ATCC Accession No. VR 2106.

2. An attenuated pseudorabies virus designated S-PRV-002 and deposited under ATCC Accession No. VR 2107.

3. A vaccine for pseudorabies virus disease which comprises an effective immunizing amount of the attenuated pseudorabies virus of claim 1 and a carrier.

4. A method of immunizing an animal against pseudorabies virus disease which comprises administering to an animal an effective immunizing dose of the vaccine of claim 3.

5. A vaccine for pseudorabies virus disease which comprises an effective immunizing amount of the attenuated pseudorabies virus of claim 2 and a carrier.

6. A method of immunizing an animal against pseudorabies virus disease which comprises administering to an animal an effective immunizing dose of the vaccine of claim 5.

7. A vaccine of claim 3 or 5, wherein the carrier is a physiologically balanced culture medium containing stabilizing agents.

8. A vaccine of claim 3 or 5, wherein the effective immunizing amount is from about $10^3$ to about $10^9$ pfu/dose.

9. A vaccine of claim 8, wherein the effective immunizing amount is from about $10^4$ to about $10^6$ pfu/dose.

10. A method of claim 4 or 6, wherein the animal is a swine, dog, cat, sheep or bovine animal.

11. A method of claim 4 or 6, wherein the vaccine is administered by intramuscular, subcutaneous, interperitoneal or intravenous injection.

12. A method of claim 4 or 6, wherein the vaccine is administered intranasally.

13. A method of claim 4 or 6, wherein the vaccine is administered orally.

* * * * *